United States Patent
Czarnik et al.

(10) Patent No.: US 10,731,116 B2
(45) Date of Patent: *Aug. 4, 2020

(54) ALCOHOLIC COMPOSITIONS HAVING A LOWERED RISK OF ACETALDEHYDEMIA

(71) Applicant: Deuteria Beverages, LLC, Reno, NV (US)

(72) Inventors: Anthony W. Czarnik, Reno, NV (US); Jeffrey A. McKinney, Lafayette, CA (US)

(73) Assignee: Deuteria Beverages, LLC, Reno, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 16/103,016

(22) Filed: Aug. 14, 2018

(65) Prior Publication Data

US 2019/0062680 A1 Feb. 28, 2019

Related U.S. Application Data

(60) Continuation of application No. 15/676,351, filed on Aug. 14, 2017, now Pat. No. 10,047,330, which is a continuation of application No. 14/726,586, filed on May 31, 2015, now Pat. No. 9,732,311, which is a division of application No. 14/153,879, filed on Jan. 13, 2014, now Pat. No. 9,044,423, which is a division of application No. 12/777,238, filed on May 10, 2010, now Pat. No. 8,658,236.

(60) Provisional application No. 61/283,524, filed on Dec. 4, 2009, provisional application No. 61/280,860, filed on Nov. 9, 2009, provisional application No. 61/274,875, filed on Aug. 21, 2009.

(51) Int. Cl.

| | |
|---|---|
| *C12G 3/08* | (2006.01) |
| *A61K 9/00* | (2006.01) |
| *A61K 9/08* | (2006.01) |
| *A61K 47/10* | (2017.01) |
| *C12C 12/00* | (2006.01) |
| *C12G 1/00* | (2019.01) |
| *C12G 3/04* | (2019.01) |
| *A61K 31/045* | (2006.01) |

(52) U.S. Cl.
CPC .............. *C12G 3/08* (2013.01); *A61K 9/0095* (2013.01); *A61K 9/08* (2013.01); *A61K 31/045* (2013.01); *A61K 47/10* (2013.01); *C12C 12/00* (2013.01); *C12G 1/00* (2013.01); *C12G 3/04* (2013.01); *A23V 2002/00* (2013.01)

(58) Field of Classification Search
CPC ................... C12G 3/00; A61K 9/00
See application file for complete search history.

(56) References Cited

U.S. PATENT DOCUMENTS

| | | | |
|---|---|---|---|
| 5,223,269 A | 6/1993 | Liepins | |
| 5,858,375 A * | 1/1999 | Furminger | ............ A61K 47/02 424/204.1 |
| 5,895,660 A | 4/1999 | Hoffmann | |
| 6,376,531 B1 | 4/2002 | Bell | |
| 2007/0082929 A1 | 4/2007 | Gant | |
| 2008/0145507 A1 * | 6/2008 | Soloviev | ................ C12C 5/002 426/592 |
| 2009/0046823 A1 * | 2/2009 | Edwards | ................ H05H 3/06 376/114 |

FOREIGN PATENT DOCUMENTS

| | | |
|---|---|---|
| WO | 95/18545 A1 | 7/1995 |
| WO | 26325 A2 | 10/1995 |

OTHER PUBLICATIONS

Kristen C. Buteau, Deuterated Drugs: Unexpectedly nonobious. (Year: 2009).*
Kushner, D.J.; Pharmacological Uses and Perspectives of Heavy Water and Deuterated Compounds; Canadian Journal of Physiology and Pharmacology 1999, 77(2), 79-88.
Buteau, Kristen C., Deuterated Drugs: Unexpectedly Unobvious?, 10 J. High Teck 22 (2009).
Bengsch, E et al., Isotopic Analysis of Mixtures of Deuterated Ethanols C2H5-nDnOH, Organic Magnetic Resonance 1974, 6, 195-9.
Cronholm, T., Incorporation of the 1-pro-R and 1-pro-S Hydrogen Atoms of Ethanol in Reduction of Acids in the Liver of Rats and in Isolated Hepatocytes, J. Biochem. 1985, 229, 323-31.
Nagano, T. et al., A New Method for the Determination of Ethanol in the Blood and Urine by Pulse Heating, Nihon Hoigaku Zasshi Aug. 1989, 43(4), 315-21.
P54301EP-K Extended European Search Report, dated Aug. 22, 2013 (related patent application in the EPO).
Cronholm, T. et al., Mechanism and Regulation of Ethanol Elimination in Humans Intermolecular Hydrogen Transfer and Oxidoreduction In-Vivo, Alcoholism Clinical and Experimental 1988, 12(5), 683-86.
Ekstroem, G.. et al., Cytochrome P 450-Dependent Ethanol Oxidation. Kinetic Isotope Effects and Absence of Stereoselectivity, Biochemistry 1987, 26(23), 7348-54.

(Continued)

*Primary Examiner* — Michael G. Hartley
*Assistant Examiner* — Jagadishwar R Samala
(74) *Attorney, Agent, or Firm* — Vance Intellectual Property PC

(57) ABSTRACT

The present invention provides beverages and pharmaceutical compositions containing a deuterated alcohol according to Formula 1, and provides methods for their manufacture and use.

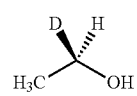

The compositions of the invention are expected to ameliorate some of the negative side effects associated with the consumption of alcohol, such as hangover and facial flushing.

16 Claims, 1 Drawing Sheet

(56) References Cited

OTHER PUBLICATIONS

Lundquist, F. et al., Deuterium Isotop Effects on Ethanol Oxidation in Perfused Rat Liver and in Rats and Rabbits in Vivo: Application to Determine the Contribution of Various Pathways, Pharmacology and Toxicology 1989, 65(1), 55-62.

Lands W. E. M., A Review of Alcohol Clearance in Humans, Alcohol 1998, 15(2), 147-60.

"Organic chemistry", Peizhou NI, pp. 422-423, People's Medical Publishing House, Nov. 30, 1999.

Translation of Office Action in Chinese Patent Application No. 201310226344.X, dated Apr. 9, 2014 (a corresponding Chinese patent application).

Kenneth Couchman, "Ethanol Metabolism in Humans", Doctor of Philosophy Thesis at Massey University, New Zealand, 1979.

English Summary of Mar. 24, 2014 Notice of Rejection in Japanese Patent Application No. 2012-525737, (this is the corresponding Japanese patent application).

\* cited by examiner

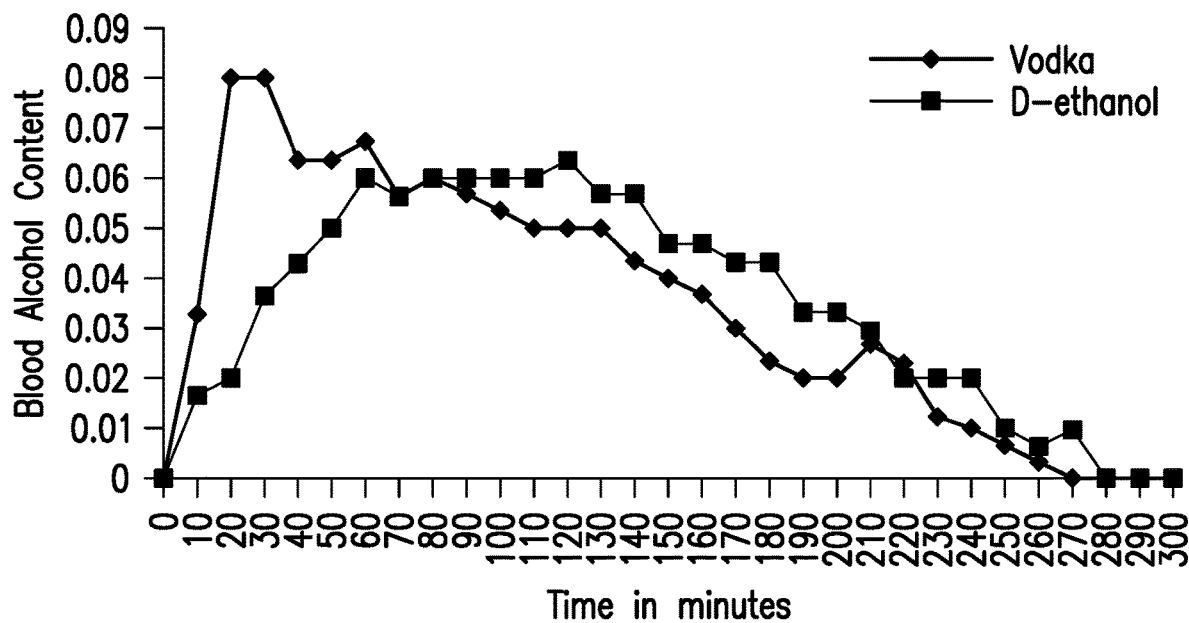

ALCOHOLIC COMPOSITIONS HAVING A LOWERED RISK OF ACETALDEHYDEMIA

CROSS-REFERENCE TO RELATED APPLICATIONS

The present application claims priority benefit under 35 U.S.C. § 119(e) of U.S. Provisional Patent Application Ser. Nos. 61/274,875 filed 21 Aug. 2009; No. 61/280,860 filed 9 Nov. 2009; and, 61/283,524 filed 4 Dec. 2009. The disclosure these applications are incorporated herein by reference.

FIELD OF THE INVENTION

The present invention is generally related to compositions and methods that diminish the negative side effects associated with the consumption of ethanol. It is more specifically related to beverages and pharmaceutical compositions containing deuterated alcohol, and the uses thereof.

BACKGROUND OF THE INVENTION

Ethanol is the principal psychoactive constituent in alcoholic beverages, which are usually consumed with the specific intent of experiencing some of ethanol's effects on the central nervous system. These effects decrease over the course of a few hours, as the ethanol is gradually metabolized by the body into acetyl CoA, a common metabolic product and energy source.

Metabolism of ethanol in the human body is a two-step process (Equation 1), mediated by the enzymes alcohol dehydrogenase (ADH) and aldehyde dehydrogenase (ALDH). Unfortunately for the consumer, the immediate metabolite of ethanol, acetaldehyde, is toxic, mutagenic, and carcinogenic.

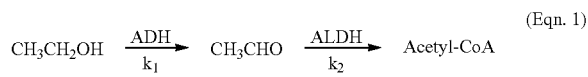

$$CH_3CH_2OH \xrightarrow[k_1]{ADH} CH_3CHO \xrightarrow[k_2]{ALDH} \text{Acetyl-CoA} \quad \text{(Eqn. 1)}$$

It can be seen from Equation 1 that when the rate of the ALDH-catalyzed reaction ($k_2$) is not high enough to keep pace with the rate of the ALD-catalyzed dehydrogenation of ethanol ($k_2$), acetaldehyde will accumulate. High acute concentrations of acetaldehyde in vivo (acetaldehydemia) can lead to undesirable effects such as cardiovascular complications, drowsiness, nausea, headache, asthma and facial flushing, while chronic acetaldehydemia can lead to cirrhosis and esophageal cancer. Another unfortunate result of acute acetaldehyde toxicity, well known to heavy drinkers, is the hangover. A person with a hangover will experience dizziness, fatigue, headache, nausea, muscle aches, vomiting, sensitivity to bright light, or sensitivity to noise, and most often a combination of these unpleasant symptoms, for a period of time typically lasting from 12 to 36 hours.

It is well established that acetaldehyde is the culprit in hangovers and in alcohol-induced facial flushing, and it is the principal suspect in alcohol-associated cancers as well vide infra. Acetaldehydemia can occur as a result of heavy alcohol consumption, leading to saturation of ALDH activity, or as a result of light or moderate alcohol consumption in the presence of abnormally high ADH activity or inadequate ALDH activity ($k_1 \gg k_2$ in Equation 1). Inherited defects in both enzyme systems are known to lead to acetaldehydemia-related syndromes. (D. W. Crabb, M. Matsumoto, D. Chang, M. You, Proc. Nutr. Soc. 2004, 63:49-63.)

For example, acetaldehydemia-related facial flushing after light drinking, or upon administration of ethanol-containing pharmaceutical compositions, is experienced by individuals possessing inactive or inefficient aldehyde dehydrogenase (ALDH). (S. Harada, D. P. Agarwal, H. W. Goedde, Lancet. 1981, 2:982.) Inhibition of ALDH by the drug disulfiram creates a similar sensitivity in people having an otherwise normally-acting enzyme. In both cases, there is a reduction of $k_2$ in Equation 1, resulting in a failure to clear acetaldehyde from the blood as rapidly as it is formed, allowing its concentration to reach toxic levels. This type of sensitivity to alcohol-induced flushing is usually associated with the ALDH2*2 allele; possession of which also enhances the risk for esophageal cancer among drinkers. (T. Yokoyama et al., Cancer Epidemiology, Biomarkers & Prevention 2003, 12:1227-1233).

Another means by which ethanol consumption may result in acetaldehydemia is by excessively rapid metabolism of ethanol (i.e., by increasing $k_1$ in Equation 1). Several studies have shown that the presence of ADH2*2 alleles, which encode hyper-active forms of alcohol dehydrogenase (W. F. Bosron, T. K. Li, Hepatology, 1986 6:502-510), also contributes to alcohol flushing and a predisposition to esophageal cancer (A. Shibuya et al., Hum. Genet. 1989, 82:14-16; T. Takeshita et al., Hum. Genet. 1996, 97: 409-413; W. J. Chen et al., Alcohol. Clin. Exp. Res. 1998, 22:1048-1052; A. Yokoyama et al., Alcohol. Clin. Exp. Res. 1999, 23:1705-1710).

From the earliest hangover, people have struggled to find an effective way to treat the disagreeable physical consequences of excessive alcohol consumption. Consumption of additional alcohol is among the oldest of remedies; the expression "Hair of the Dog" has been attributed to the $4^{th}$ century B.C. Greek playwright Antiphanes. (E. C. Brewer, Dictionary of Phrase and Fable, 1898). While this may temporarily alleviate the symptoms of acetaldehydemia and alcohol withdrawal, it merely postpones the misery and is likely to compound the damage. Other supposedly effective interventions have included a wide variety of foods, vitamins, dietary supplements, exercises and pharmaceuticals. Compounds intended to sequester acetaldehyde in vivo have been designed and evaluated (see, e.g., H. T. Nagasawa et al., J. Med. Chem. 1987, 30:1373-1378), and a wide array of unproven "supplements" and nutraceuticals are marketed to the public as hangover treatments. Notwithstanding the vast trove of folklore and anecdotal evidence, none of these methods has ever been shown to be effective in a clinical trial. (M. H. Pittler et al., BMJ, 2005, 331:1515-1518.)

The alcohol-induced flush reaction (sometimes called "Asian flush" because of its relatively greater occurrence among those of Asian descent) is a set of symptoms experienced by a person having an enzyme abnormality related to the metabolism of ethanol. When an affected person consumes alcohol, there is a rapid build-up of acetaldehyde in his system, due to an aldehyde dehydrogenase deficiency and/or an excess of alcohol dehydrogenase activity. This build-up causes erythema (reddening due to capillary dilation) of the face, neck, and shoulder of the person; the person may also experience nausea, headaches, light-headedness, and an increased pulse rate. The sensations are sufficiently unpleasant that the affected individuals frequently refrain from drinking entirely, and they may be discouraged from the use of ethanol-containing pharmaceuticals. Drugmakers wishing to address this problem have had to surrender ethanol's advantageous physical properties, low cost, and relative safety. As with hangovers, there remains a need for compositions and methods that reliably address the problem of ethanol-induced flushing.

The deuterium isotope effect is a well-known phenomenon in the fields of enzymology and pharmacodynamics. The primary isotope effect can be especially large, and deuterium substitution of enzymatically-removed hydrogens can slow the rate of metabolism of substrates in vivo by a factor of two or three. In particular, it is well-established that appropriate deuteration of a substrate, by slowing the rate of metabolism, can reduce the concentration of metabolites in vivo. An early and pertinent example is the effect of deuteration of the N-methyl group of morphine: metabolism in vivo is slowed by a factor of about two, lowering the blood level of the pharmacologically active metabolite and causing a corresponding reduction in analgesic potency (C. Elison et al., *Science*, 1961, 1078-1079).

Deuterated drugs have been the subject of a number of patent applications. U.S. Pat. No. 5,223,269 to Liepins describes methods and compositions for treating hypertension. U.S. Pat. No. 5,838,375 to Furminger describes pharmaceutical compositions containing a biological agent and $D_2O$ to improve the stability of the agent. U.S. Pat. No. 5,895,660 to Hoffmann describes deuterated drugs for transdermal applications. U.S. Pat. No. 6,376,531 describes deuterated pharmaceuticals for the treatment of psychiatric disorders. The contents of these patents are incorporated by reference into this document in their entirety, for all purposes.

The hydrogen atoms at C-1 in ethanol are enantiotopic; by convention the oxygen and the C-1 and C-2 carbons define a plane which divides the surrounding space, and the hydrogen residing in the "Si" half-space is specified as H(Si) or $H_{Si}$. The hydrogen in the "Re" half-space is designated as H(Re) or $H_{Re}$. In the case of ethanol, an alternative terminology designates $H_{Re}$ as the "pro-R" hydrogen, and $H_{Si}$ as "pro-S". The absolute stereochemistry is shown below:

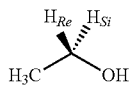

In the course of oxidation by a mammalian alcohol dehydrogenase, $H_{Re}$ of ethanol is stereospecifically removed and transferred to the enzyme cofactor NAD, with concurrent abstraction of the hydroxyl proton. This produces acetaldehyde as the product, in which $H_{Si}$ has been retained as the aldehydic hydrogen.

Remarkably, despite thousands of years of effort directed to lessening the unpleasant effects of excess ethanol consumption, and more recent attempts to alleviate problems associated with administration of ethanol-containing pharmaceutical formulations, there is still a need for compositions and methods that effectively address these problems.

SUMMARY OF THE INVENTION

The present invention provides an alcoholic composition, such as a beverage or a pharmaceutical formulation, wherein at least 5 mole percent of the ethanol in the composition is deuterated ethanol wherein $H_{Re}$ is deuterium, as shown in Formula 1.

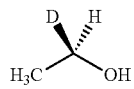

Formula 1

It should be understood that in Formula 1, and in all other structures represented herein, each atom designated "H" without a superscript may independently be hydrogen ($^1H$) or deuterium ($^2H$). The terms "$^2H$" and "D" are used interchangeably to refer specifically to deuterium.

The present invention also provides methods for increasing the time period between the consumption of an alcoholic beverage and the attainment of peak blood levels of ethanol, and methods for delaying the onset of ethanol-induced symptoms associated with the consumption of alcoholic beverages, which comprise the consumption of an alcoholic beverage containing a deuterated ethanol. The invention also provides methods for ameliorating acetaldehydemia and its symptoms, which comprise the consumption of the alcohol-containing beverages and pharmaceutical compositions of the invention.

BRIEF DESCRIPTION OF THE FIGURE

FIG. 1 shows the time course of blood alcohol levels in a human subject after administration of ordinary beverage ethanol (♦) and 1,1-dideuterioethanol (■).

DETAILED DESCRIPTION OF THE INVENTION

The present invention takes advantage of the surprising discovery that the rate of absorption of orally-administered ethanol in a human subject is significantly reduced if the ethanol is deuterated (FIG. 1). Peak blood concentrations of ethanol, which normally are reached 20-30 minutes after ingestion, are delayed to 1-2 hours after ingestion, and peak concentrations are reduced by 15-20%. (The biochemical basis for this unexpected sensitivity to molecular weight is not presently known.) Peak acetaldehyde blood levels are delayed and reduced as well, because the rate of oxidation by alcohol dehydrogenase is a function of the concentration of ethanol.

The invention provides an alcoholic composition, such as a beverage or a pharmaceutical formulation, wherein at least 5 mole percent of the ethanol in the composition is deuterated ethanol wherein $H_{Re}$ is deuterium, as shown in Formula 1:

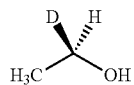

Formula 1

As noted above, each atom designated "H" may independently be hydrogen ($^1H$) or deuterium ($^2H$). Specific examples of suitable deuterated ethanols include, but are not limited to, ethanol-1-D (Formula 2), ethanol-1,1-$D_2$ (Formula 3), ethanol-1,2-$D_2$, (Formula 4), and ethanol-$D_5$ ($CD_3CD_2OH$). The enantiomer of the ethanol-1-D illustrated in formula 2 may be present in the compositions of the invention.

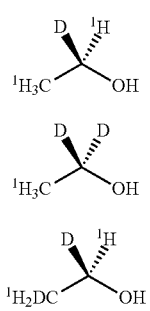

Formula 2

Formula 3

Formula 4

In successively more-preferred embodiments, the compositions comprise ethanol wherein at least 15 mole percent, 30 mole percent, 50 mole percent, 75 mole percent, or 95 mole percent of the ethanol is a deuterated alcohol according to Formula 1.

In additional embodiments, the present invention also takes advantage of the fact that the removal of $H_{Re}$ from ethanol by alcohol dehydrogenase is subject to a substantial primary deuterium isotope effect. Specifically, a deuterium ($^2H$) in the $H_{Re}$ position is removed by alcohol dehydrogenase two to four times more slowly than a light ($^1H$) hydrogen. This effect has been thoroughly documented both in vitro (B. V. Plapp et al., *J. Biol. Chem.* 1973, 248:3470; Lundquist et al., *Alcohol Clin. Exp. Res.* 1986, 10 (6th Suppl):69S-72S; J. O. Winberg et al., *Biochem. Mol. Biol. Int.* 1993, 31:651-658) and in vivo (S. E. Damgaard, *Biochemistry* 1981, 20:5662-5669; J. Alderman et al., *J. Biol. Chem.* 1987, 262:7497-7503; F. Lundquist et al., *Pharmacol. Toxicol.* 1989 65:55-62).

Due to the primary deuterium isotope effect, an individual having a greater-than-normal level of alcohol dehydrogenase activity, and consequently having a propensity to alcohol-induced flushing, upon consumption of an alcoholic composition of the invention, should metabolize the deuterated ethanol of Formula 1 at a significantly slower rate than he or she would metabolize ethanol having a natural isotopic abundance at $H_{Re}$. Because the kinetic isotope effect produces a lowering of $k_1$ in Equation 1, the individual's rate of production of acetaldehyde in vivo should be shifted back toward the rate observed in normal individuals. The result should be a reduced level of acetaldehyde in the individual's system, with a corresponding reduction in the severity of symptoms of acetaldehydemia, such as hangover and alcohol-induced flushing. The greater the proportion of deuterium at $H_{Re}$ in the ethanol, the greater the expected reduction in acetaldehyde concentration in the blood.

The reduction in acetaldehyde blood levels should be especially pronounced if the individual can metabolize the ADH-generated acetaldehyde at a rate that prevents accumulation of the aldehyde. The metabolism of acetaldehyde to acetate is carried out by aldehyde dehydrogenase (ALDH), and to a certain extent by cytochrome P450. Some ALDH enzymes exhibit a deuterium isotope effect when operating on certain substrates, such as benzaldehydes (M. Scharschmidt et al., *Biochemistry* 1984, 23:5471-5478) and glyceraldehyde-3-phosphate (P. F. Canellas and W. W. Cleland, *Biochemistry* 1991, 30:8871-8876). On the other hand, sheep liver ALDH shows no isotope effect when acting upon acetaldehyde-1-d ($CH_3CDO$) (G. J. Hart and F. M. Dickinson, *Biochem. J.* 1978, 175:899-908), and horse liver ALDH shows no isotope effect when acting upon propionaldehyde-1-d ($CH_3CH_2CDO$) (R. I. Feldman and H. Weiner, *J. Biol. Chem.* 1972, 247:267-272). In order to avoid any possible reduction in ALDH activity, it can be desirable to have little or no deuterium at $H_{Si}$ in the compound of Formula 1, and correspondingly little or no production of $CH_3CDO$. It should however be understood that lowering the in vivo acetaldehyde concentration by providing deuterium at $H_{Re}$ of ethanol, by the methods of the present invention, should reduce the symptoms of acetaldehydemia regardless of the isotopic composition of $H_{Si}$.

It will be appreciated that even in individuals not suffering from an enzyme abnormality, consumption of the compositions of the invention in place of equivalent prior art beverages and pharmaceutical formulations should still lead to slower formation of acetaldehyde in vivo, with attendant reduction of the symptoms of acetaldehydemia. The slower metabolism of the deuterated alcohol of the invention, in combination with the extended period of peak blood alcohol concentration, should reduce the amount of alcohol needed to produce a given psychopharmacological effect. The beverages of the present invention, accordingly, can be manufactured with a lower alcohol content than equivalent prior art beverages without being perceived by consumers as "weaker" or less potent, and they should produce a more consistent and prolonged effect with a less-pronounced initial effect. In particular, the beverages of the invention may be consumed on an empty stomach, with less risk of a sudden onset of inebriation.

Conversely, pharmaceutical compositions can be produced having higher ethanol concentrations and greater solvent power than prior art compositions, without an increase in acetaldehyde-induced side-effects. The greater solvent power enables the production of more concentrated formulations, with attendant savings and convenience.

The present invention thus provides methods for avoiding, or reducing the severity of, ethanol-induced acetaldehydemia, hangover and facial flushing, by providing and/or consuming the alcoholic beverages and pharmaceutical compositions of the invention.

The present invention also provides a method of making an alcoholic beverage. The method comprises the step of adding to a beverage a deuterated alcohol according to Formula 1, in an amount sufficient to produce an alcoholic beverage comprising water and ethanol wherein at least 5 mole percent of the ethanol is a deuterated alcohol according to Formula 1. In additional embodiments, a deuterated alcohol according to Formula 1 is added in an amount sufficient to produce an alcoholic beverage comprising water and ethanol wherein at least 15 mole percent, 30 mole percent, 50 mole percent, 75 mole percent, or 95 mole percent of the ethanol is a deuterated alcohol according to Formula 1.

The present invention also provides a method of making an alcoholic pharmaceutical composition. The method comprises the step of combining an active pharmaceutical ingredient (API) with a deuterated alcohol according to Formula 1, in an amount sufficient to produce a composition wherein at least 5 mole percent of the ethanol in the composition is a deuterated alcohol according to Formula 1. In additional embodiments, the deuterated alcohol according to Formula 1 is combined in an amount sufficient to produce a composition wherein at least 15 mole percent, 30 mole percent, 50 mole percent, 75 mole percent, or 95 mole percent of the ethanol in the composition is a deuterated alcohol according to Formula 1. Pharmaceutically acceptable excipients may be introduced or admixed with the deuterated ethanol and/or the API, prior to or following the combining step.

In the present document, the use of "H" refers to the genus of hydrogen atoms, of any isotopic composition, i.e. $^1$H, $^2$H, or any combination thereof in any proportions. The use of "D" or "$^2$H" refers specifically to the deuterium isotope. Proportions described herein by percentages are percent by weight unless otherwise indicated.

"Alcohol" refers to ethanol.

"Alcopop" refers to certain flavored alcoholic beverages, including: malt beverages to which various fruit juices or other flavorings have been added; beverages containing wine to which ingredients such as fruit juice or other flavorings have been added (e.g., wine coolers); and beverages containing distilled alcohol and added ingredients such as fruit juices or other flavorings.

"Almost sake" refers to sake infused with fruit flavors. One example of "almost sake" is Hana flavored sake produced by Takara Sake.

"Awamori" refers to a distilled spirit derived from long grain rice that is typically made in Okinawa.

"Baijiu" refers to a distilled spirit made from sorghum, wheat or glutinous rice. It typically has an alcohol content of about 60%.

"Beer" refers to an alcoholic beverage produced by the brewing and fermentation of starches, which are primarily derived from cereal grains (e.g., malted barley, wheat, corn and rice). The alcohol content of beer typically ranges from one percent to six percent.

"Alcoholic beverage" refers to a liquid suitable for human consumption, which contains ethanol, water, and at least one additional component, which is a sweetener, odorant, or flavorant, or a congener derived from the brewed or fermented compositions from which the beverage is produced. The amount of ethanol is at least 1% by weight. In various other embodiments of the invention, the amount of ethanol is at least 2%, 5%, 10%, 20%, or 40% by weight. "Deuterated alcohol," in the context of this document, refers to ethanol having at least one deuterium atom, and corresponding to Formula 1. Deuterated alcohols are articles of commerce sold by vendors such as CDN Isotopes, Inc., Pointe-Claire, Quebec, Canada, and methods for making such compounds are well known to those of skill in the art. Ethanol stereospecifically deuterated at the $H_{Re}$ position is known (see Damgaard et al., *Biochemistry*, 1981 20:5662-9, and references therein), while racemic ethanol-1-d is readily obtained by reduction of acetaldehyde with $BD_3$ or $NaBD_4$. Non-specific hydrogen-deuterium exchange reactions are referenced and/or discussed in U.S. Pat. No. 7,517,990, which is incorporated by reference into this document in its entirety for all purposes, and particularly for the purpose of disclosing methods of deut$_{er}$ium incorporation. Hydrogenation of a vinyl ester (e.g., vinyl acetate) with $D_2$ gas, followed by hydrolysis, will provide ethanol-1,2-$d_2$ having at least 50% D at the $H_{Re}$ position, the proportion of D at this position may be raised, if desired, by the use of an asymmetric hydrogenation catalyst. (See, e.g., G. J. Clarkson et al., *Tetrahedron: Asymmetry*, 2004, 15:1787-1792.)

"Enzyme abnormality" in the context of metabolism of ethanol refers to either a decreased aldehyde dehydrogenase level or an increased level of activity of alcohol dehydrogenase, or both, which results in higher than normal levels of acetaldehyde in the body of an affected person. Although this is most commonly the result of allelic variations in the genes encoding the enzymes, other causes (e.g. misregulation of gene expression) are encompassed by the present invention.

References herein to methods of "avoiding" or "reducing the severity" of symptoms of acetaldehydemia should be understood to refer to an avoidance or reduction relative to the symptoms that would be experienced with an equivalent dose of a non-deuterated composition.

"Fermentation byproduct" refers to non-ethanol compounds produced as the result of starch fermentation.

"Han" refers to a liquor made from barley vodka that has been distilled multiple times and mixed with polished rice. It is not diluted with water.

"Pharmaceutical composition" refers to a liquid composition, suitable for administration to humans, comprising an active pharmaceutical ingredient, ethanol, and optionally water and/or other pharmaceutically acceptable excipients.

"Sake" refers to an alcohol-based drink produced by multiple, parallel fermentation of polished rice. There are two basic types of sake: futsu-shu, which is oftentimes referred to as "ordinary sake"; and, tokutei meisho-shu, which is a premium sake oftentimes referred to as "special designation sake". Honjozo-shu, Junmai-shu and Ginjo-shu are categories of premium sake. Honjozo-shu includes a processing step of adding a slight amount of brewer's alcohol to sake before pressing. Junmai-shu, or "pure rice sake", is made simply from rice, water and koji mold (*Aspergillus oryzae*); no brewer's yeast or other additives are included in the production process. Ginjo-shu is made from rice that has been polished to 60% or less of its original weight.

"Shochu" refers to a distilled spirit made from barley, sweet potatoes, cane sugar, or rice. It typically has an alcohol content of 25% or more.

"Soju" refers to a distilled spirit traditionally made from rice with an alcohol content ranging from 25% to 45%. In some varieties, the manufacturing process involves the fermentation of potatoes, barley, wheat, sweet potatoes or tapioca instead of rice.

"Spirits" refers to alcoholic beverages produced by the fermentation of starches and subsequent distillation. The starches are usually derived from a variety of natural sources (e.g., agave, potato, beets, un-malted cereal grain), and spirits typically have an alcohol content greater than twenty percent. The term encompasses distilled spirits such as vodka, gin, whisky, rye, cognac, brandy, bourbon, rum, tequila, and the like.

"Wine" refers to an alcoholic beverage produced by the fermentation of sugars and starches, primarily derived from fruits (e.g., grapes). The alcohol content of wine typically ranges from nine percent to sixteen percent. Fortified wines, having higher alcohol content, are encompassed within the term as well.

Compositions

Compositions of the present invention are beverages and pharmaceutical formulations that comprise a deuterated alcohol according to Formula 1. Typically, the compositions comprise between 0.25 percent and 60.0 percent by weight of the deuterated alcohol.

Where the beverage is an alcopop, it typically comprises between 0.25 percent and 20.0 percent of the deuterated alcohol. Oftentimes, the beverage comprises between 0.5 percent and 15.0 percent of the deuterated alcohol. In specific cases, the beverage may comprise any of the following ranges of deuterated alcohol: 1.0 percent to 15.0 percent; 2.0 percent to 15.0 percent; 3.0 percent to 15.0 percent; 4.0 percent to 15.0 percent; 4.0 percent to 14.0 percent; 4.0 percent to 13.0 percent; 4.0 percent to 12.0 percent; 4.0 percent to 11.0 percent; 4.0 percent to 10.0 percent; 4.0 percent to 9.0 percent; and 4.0 percent to 8.0 percent.

Where the beverage is beer, it typically comprises between 0.25 percent and 15.0 percent of the deuterated alcohol. Oftentimes, the beverage comprises between 0.5 percent and 12.0 percent of the deuterated alcohol. In specific cases, the beverage may comprise any of the following ranges of deuterated alcohol: 1.0 percent and 12.0 percent; 2.0 percent and 12.0 percent; 3.0 percent and 12.0 percent; 3.0 percent and 11.0 percent; 3.0 percent and 10.0 percent; 3.0 percent and 9.0 percent; 3.0 percent and 8.0 percent; 3.0 percent and 7.0 percent; and, 3.0 percent and 6.0 percent.

Where the beverage is wine, it typically comprises between 0.25 percent and 15.0 percent of the deuterated alcohol. Oftentimes, the beverage comprises between 0.5 percent and 12.0 percent of the deuterated alcohol. In specific cases, the beverage may comprise any of the following ranges of deuterated alcohol: 1.0 percent and 12.0 percent; 2.0 percent and 12.0 percent; 3.0 percent and 12.0 percent; 4.0 percent and 12.0 percent; 5.0 percent and 12.0 percent; 6.0 percent and 12.0 percent; 3.0 percent and 11.0 percent; 3.0 percent and 10.0 percent; 3.0 percent and 9.0 percent; 3.0 percent and 8.0 percent; 3.0 percent and 7.0 percent; and, 3.0 percent and 6.0 percent.

Where the beverage is a spirit, it typically comprises between 20.0 percent and 60.0 percent of the deuterated alcohol. Oftentimes, the beverage comprises between 25.0 percent and 50.0 percent of the deuterated alcohol. In specific cases, the beverage may comprise any of the following ranges of deuterated alcohol: 20.0 percent to 50.0 percent; 20.0 percent to 45.0 percent; 20.0 percent to 40.0 percent; 20.0 percent to 35.0 percent; and 20.0 percent to 30.0 percent.

Where the beverage is sake, it typically comprises between 0.25 percent and 20.0 percent of the deuterated alcohol. Oftentimes, the beverage comprises between 0.25 percent and 17.5 percent of the deuterated alcohols. In certain cases, the beverage may comprise any of the following ranges of deuterated alcohol: 1.0 percent to 15.0 percent; 1.0 percent to 12.5 percent; 1.5 percent to 10.0 percent; 2.0 percent to 10.0 percent; and 2.5 percent to 10.0 percent.

Where the beverage is awamori, it typically comprises between 0.25 percent and 35.0 percent of the deuterated alcohol. Oftentimes, the beverage comprises between 0.25 percent and 30.0 percent of the deuterated alcohol. In certain cases, the beverage may comprise any of the following ranges of deuterated alcohol: 1.0 percent to 27.5 percent; 1.5 percent to 25.0 percent; 2.0 percent to 20.0 percent; 2.5 percent to 17.5 percent; and 2.5 percent to 15.0 percent.

Where the beverage is baijiu, it typically comprises between 0.25 percent and 65.0 percent of the deuterated alcohol. Oftentimes, the beverage comprises between 0.25 percent and 60.0 percent of the deuterated alcohol. In specific cases, the beverage may comprise any of the following ranges of deuterated alcohols: 1.0 percent to 55.0 percent; 1.5 percent to 50.0 percent; 2.0 percent to 45.0 percent; 2.5 percent to 40.0 percent; 3.0 percent to 35.0 percent; and 3.5 percent to 30.0 percent.

Where the beverage is han, it typically comprises between 0.25 percent and 55.0 percent of the deuterated alcohol. Oftentimes, the beverage comprises between 0.25 percent and 50.0 percent of the deuterated alcohol. In specific cases, the beverage may comprise any of the following ranges of deuterated alcohol: 1.0 percent to 45.0 percent; 1.5 percent to 40.0 percent; 2.0 percent to 35.0 percent; 2.5 percent to 30.0 percent; and 3.0 percent to 25.0 percent.

Where the beverage is shochu, it typically comprises between 0.25 percent and 35.0 percent of the deuterated alcohol. Oftentimes, the beverage comprises between 0.25 percent and 30.0 percent of the deuterated alcohol. In specific cases, the beverage may comprise any of the following ranges of deuterated alcohol: 1.0 percent to 25.0 percent; 1.5 percent to 22.5 percent; 2.0 to 20.0 percent; 2.5 percent to 17.5 percent; 3.0 percent to 15.0 percent; and 3.5 percent to 12.5 percent.

Where the beverage is soju, it typically comprises between 0.25 percent and 50.0 percent of the deuterated alcohol. Oftentimes, the beverage comprises between 0.25 percent and 45.0 percent of the deuterated compound. In specific cases, the beverage may comprise any of the following ranges of deuterated alcohol: 1.0 percent to 40.0 percent; 1.5 percent to 35.0 percent; 2.0 percent to 30.0 percent; 2.5 percent to 25.0 percent; and 2.5 percent to 20.0 percent.

Where the beverage is almost sake, it typically comprises between 0.25 percent and 12.0 percent of the deuterated alcohol. Oftentimes, the beverage comprises between 0.25 percent and 11.0 percent of the deuterated alcohol. In specific cases, the beverage may comprise any of the following ranges of deuterated alcohol: 1.0 percent to 10.0 percent; 1.5 percent to 9.0 percent; 2.0 percent to 8.0 percent; 2.5 percent to 7.5 percent; 3.0 percent to 7.0 percent; and 3.5 percent to 6.0 percent.

The various beverages include mixtures of non-deuterated ethanol and a deuterated ethanol of Formula 1, usually in ratios ranging from 1/10 to 10/1. The non-deuterated ethanol can be obtained, for instance, from compositions derived from fermentation, brewing and fermentation, and/or fermentation and subsequent distillation.

For instance, where the beverage is an alcopop containing both deuterated and non-deuterated ethanol, non-limiting examples of deuterated to non-deuterated alcohol mixture ratios, by weight, include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is beer containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is wine containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is a spirit containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is sake containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is awamori containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is baijiu containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is han containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is shochu containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is soju containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

Where the beverage is almost sake containing both deuterated and non-deuterated ethanol, non-limiting examples of deuterated to non-deuterated alcohol mixture weight ratios include: 1/10; 1/9; 1/8; 1/7; 1/6; 1/5; 1/4; 1/3; 1/2; 1/1; 2/1; 3/1; 4/1; 5/1; 6/1; 7/1; 8/1; 9/1; and, 10/1.

EXAMPLES

By way of illustration, representative examples of various beverages according to the present invention are provided below.

Example 1

Beverage type: alcopop.
Total ethanol content (deuterated and non-deuterated): 4.0 percent to 8.0 percent.
Percentage of deuterated ethanol: 100 percent.
Percentage of non-deuterated ethanol: 0 percent.
Other ingredients: water; sugar; fruit juice and/or soda.

Example 2

Beverage type: alcopop.
Total ethanol content (deuterated and non-deuterated): 4.0 percent to 8.0 percent.
Percentage of deuterated ethanol: 90 percent.
Percentage of non-deuterated ethanol: 10 percent.
Other Ingredients: water; sugar; fruit juice and/or soda.

Example 3

Beverage type: alcopop.
Total ethanol content (deuterated and non-deuterated): 4.0 percent to 8.0 percent.
Percentage of deuterated ethanol: 80 percent.
Percentage of non-deuterated ethanol: 20 percent.
Other ingredients: water; sugar; fruit juice and/or soda.

Example 4

Beverage type: alcopop.
Total ethanol content (deuterated and non-deuterated): 4.0 percent to 8.0 percent.
Percentage of deuterated ethanol: 70 percent.
Percentage of non-deuterated ethanol: 30 percent.
Other ingredients: water; sugar; fruit juice and/or soda.

Example 5

Beverage type: alcopop.
Total ethanol content (deuterated and non-deuterated): 4.0 percent to 8.0 percent.
Percentage of deuterated ethanol: 60 percent.
Percentage of non-deuterated ethanol: 40 percent.
Other ingredients: water; sugar; fruit juice and/or soda.

Example 6

Beverage type: alcopop.
Total ethanol content (deuterated and non-deuterated): 4.0 percent to 8.0 percent.
Percentage of deuterated ethanol: 50 percent.
Percentage of non-deuterated ethanol: 50 percent.
Other ingredients: water; sugar; fruit juice and/or soda.

Example 7

Beverage type: alcopop.
Total ethanol content (deuterated and non-deuterated): 4.0 percent to 8.0 percent.
Percentage of deuterated ethanol: 40 percent.
Percentage of non-deuterated ethanol: 60 percent.
Other ingredients: water; sugar; fruit juice and/or soda.

Example 8

Beverage type: alcopop.
Total ethanol content (deuterated and non-deuterated): 4.0 percent to 8.0 percent.
Percentage of deuterated ethanol: 30 percent.
Percentage of non-deuterated ethanol: 70 percent.
Other ingredients: water; sugar; fruit juice and/or soda.

Example 9

Beverage type: alcopop.
Total ethanol content (deuterated and non-deuterated): 4.0 percent to 8.0 percent.
Percentage of deuterated ethanol: 20 percent.
Percentage of non-deuterated ethanol: 80 percent.
Other ingredients: water; sugar; fruit juice and/or soda.

Example 10

Beverage type: alcopop.
Total ethanol content (deuterated and non-deuterated): 4.0 percent to 8.0 percent.
Percentage of deuterated ethanol: 10 percent.
Percentage of non-deuterated ethanol: 90 percent.
Other ingredients: water; sugar; fruit juice and/or soda.

Example 11

Pharmaceutical composition: Aromatic Elixir, U.S.P.
Total ethanol content (deuterated and non-deuterated): 22 percent.
Percentage of deuterated ethanol: 90 percent.
Percentage of non-deuterated ethanol: 10 percent.
Other ingredients: water, sugar, orange oil, lemon oil, coriander oil, and anise oil.

By way of example, the following pharmaceutical compositions may be prepared substantially as is currently known in the art, but with substitution of a deuterated ethanol of Formula 1 for 50% to 100% of the total ethanol in the composition:

| Brand name | API | Ethanol content (%) |
|---|---|---|
| Anbesol ™ | benzocaine (20%) | 70 |
| Asbron G ™ Elixir | guaifenesin (6.7 mg/ml) theophylline glycinate (20 mg/ml) | 15 |
| Diphenhydramine Elixir | diphenhydramine HCl (2.5 mg/ml) | 14 |
| Bronkolixir ™ | ephedrine sulfate (2.4 mg/ml) guaifenesin (10 mg/ml) phenobarbital (0.8 mg/ml) theophylline (3 mg/ml) chlorpheniramine maleate (0.2 mg/ml) | 19 |
| Choedyl ™ Elixir | oxtriphylline (20 mg/ml) | 20 |
| CONTAC ™ Nighttime | acetaminophen (33 mg/ml) chlorpheniramine maleate (.13 mg/ml)) dextromethorphan HBr (1 mg/ml) pseudoephedrine HCl (2 mg/ml) | 25 |
| Donnatal ™ Elixir | phenobarbital (3 mg/ml) hyoscyamine sulfate (21 ug/ml) atropine sulfate (3.9 ug/ml) scopolamine HBr (1.3 ug/ml) | 23 |
| Elixophyllin ™ Elixir | theophylline (5.3 mg/ml) | 20 |
| Lasix ™ Oral Solution | furosemide (10 mg/ml) | 11.5 |
| Lomotil ™ Liquid | diphenoxylate HCl (5 mg/ml) atropine sulfate (5 ug/ml) | 15 |
| Lufyllin ™ Elixir | dyphylline (10.7 mg/ml) | 20 |
| Nicotinex ™ | niacin (10 mg/ml) | 14 |
| Nucofed ™; Tussar ™ SF | codeine phosphate (2 mg/ml) pseudoephedrine HCl (6 mg/ml) guaifenesin (20 mg/ml) | 12.5 |
| Organidin ™ Elixir | guaifenesin (40 mg/ml) dextromethorphan HBr (4 mg/ml) | 22 |
| Phenobarbital Elixir | phenobarbital (3 mg/ml) | 13.5 |
| Prolixin ™ Elixir | fluphenazine HCl (0.5 mg/ml) | 14 |
| Robitussin ™ Night Relief | acetaminophen (22 mg/ml) dextromethorphan HBr (1 mg/ml) pseudoephedrine HCl (2 mg/ml) pyrilamine maleate (1.7 mg/ml) | 25 |
| Sandimmune ™ Oral | cyclosporine (100 mg/ml) | 12.5 |
| Sominex ™ Liquid | diphenhydramine HCl (12.5 mg/ml) | 10 |
| Tussend ™ Expectorant | chlorpheniramine maleate (0.4 mg/ml) hydrocodone bitartrate (0.5 mg/ml) pseudoephedrine HCl (6 mg/ml) | 12.5 |
| Vicks Nyquil ™ | doxylamine succinate (0.4 mg/ml) acetaminophen (33 mg/ml) pseudoephedrine HCl (2 mg/ml) dextromethorphan HBr (1 mg/ml) | 25 |

Methods

The present invention provides a method of making an alcoholic beverage. The method comprises the step of adding to an alcoholic, non-alcoholic, or reduced-alcohol beverage a deuterated alcohol according to Formula 1, in an amount sufficient to produce a beverage comprising water and ethanol wherein at least 5 mole percent of the ethanol is a deuterated alcohol according to Formula 1. In another embodiment, a deuterated alcohol according to Formula 1 is added in an amount sufficient to produce a beverage comprising water and ethanol wherein at least 15 mole percent of the ethanol is a deuterated alcohol according to Formula 1. In another embodiment, a deuterated alcohol according to Formula 1 is added in an amount sufficient to produce a beverage comprising water and ethanol wherein at least 30 mole percent of the ethanol is a deuterated alcohol according to Formula 1. In another embodiment, a deuterated alcohol according to Formula 1 is added in an amount sufficient to produce a beverage comprising water and ethanol wherein between 50 and 100 mole percent of the ethanol is a deuterated alcohol according to Formula 1.

The present invention also provides a method of making an alcoholic pharmaceutical composition. The method comprises the step of adding to an active pharmaceutical ingredient a deuterated alcohol according to Formula 1, in an amount sufficient to produce, after all other ingredients have been incorporated, a pharmaceutical composition wherein at least 5 mole percent of the ethanol in the composition is a deuterated alcohol according to Formula 1. In another embodiment, a deuterated alcohol according to Formula 1 is added in an amount sufficient to produce a pharmaceutical composition wherein at least 15 mole percent of the ethanol in the composition is a deuterated alcohol according to Formula 1. In another embodiment, a deuterated alcohol according to Formula 1 is added in an amount sufficient to produce a pharmaceutical composition wherein at least 30 mole percent of the ethanol in the composition is a deuterated alcohol according to Formula 1. In another embodiment, a deuterated alcohol according to Formula 1 is added in an amount sufficient to produce a pharmaceutical composition wherein between 50 and 100 mole percent of the ethanol in the composition is a deuterated alcohol according to Formula 1.

Practitioners of the present invention will appreciate that the benefits of increasing the mole fraction of deuterated ethanol will be obtained at correspondingly higher cost, and that profitable use of the invention in commercially marketed products will entail a trade-off between benefits and costs.

Beverages according to the present invention are typically made by adding one or more of the deuterated alcohols to other ingredients. In the case of Example 6 above, for example, one could mix suitable amounts of fruit juice, water, sugar and non-deuterated ethanol (e.g., malt liquor or vodka) together, followed by the addition of the correct amount of deuterated alcohol needed to arrive at a beverage containing 4 percent to 8 percent ethanol, with 50 percent of the ethanol being deuterated alcohol.

Beer and wine beverages are typically made by adding a suitable amount of the deuterated alcohol of Formula 1 to either beer or wine that has a reduced alcohol content. For instance, if a beer is desired that has a 6 percent ethanol content, one would obtain a reduced-alcohol beer (e.g., beer containing 3.2% non-deuterated ethanol) or a non-alcoholic beer, and add an amount of deuterated ethanol such that the overall ethanol content (i.e., deuterated plus non-deuterated) is 6 percent.

Spirits are available with a variety of alcohol contents. As with beer and wine, one can make a spirit beverage according to the present invention by adding deuterated ethanol to a spirit having less than the desired amount of ethanol—e.g., adding deuterated ethanol such that the overall alcohol content of a spirit is increased from 20 percent (non-deuterated) ethanol to 40 percent.

Sake, awamori, baijiu, han, shochu, soju, and "almost sake" beverages according to the present invention are preferably made by adding a suitable amount of a deuterated alcohol of Formula 1 to a reduced-alcohol version of the beverage. For instance, if a sake is desired that has a 15 percent ethanol content, one may obtain a reduced-alcohol sake and add an amount of deuterated ethanol according to Formula 1 such that the overall ethanol content (deuterated plus non-deuterated) is 15 percent. Examples of suitable reduced-alcohol sakes include, but are not limited to, sparkling sakes such as POOCHI POOCHI™ (Junmai Sparking Sake, Suehiro Sake Brewery (Tohoku, Fukushima), alcohol content 7.5%), TANZAN JAPON™ (Junmai Sparkling Sake, Tanzan Shuzo (Kinki, Kyoto), alcohol content 8.0%), HANA AWAKA™ (Junmai Sparkling Sake, Ozeki Corporation (Kinki, Hyogo), alcohol content 7.0%), and SAWA-SAWA™ (Junmai Sparkling Sake, Choryo (Kinki, Nara), alcohol content 8.0-9.0%).

Methods of making reduced-alcohol beer and wine are also well known to those of ordinary skill in the art. Non-alcoholic and "light" beers, in particular, are well-known articles of commerce. A description related to the production of low-alcohol beer is presented in United States Patent Publication No. 20070116801 and references therein; a description regarding the production of low-alcohol wine appears in U.S. Pat. No. 4,681,767 and references therein. Both of these patent documents are incorporated by reference into this document in their entireties, for all purposes.

Methods of making reduced-alcohol sake are also well known to those of ordinary skill in the art. A description related to the production of low-alcohol sake is presented in "Development of Low Alcohol Sake" *Onko Chishin*, 2004, pp 58-62.

A method of producing low-alcohol beverages which has general applicability is discussed in U.S. Pat. No. 4,612,196 ("Preparation of Low Alcohol Beverages by Reverse Osmosis"), which is incorporated by reference into this document in its entirety, for all purposes.

The present invention provides a method of reducing the severity of a hangover in a person to whom the practitioner is serving alcoholic beverages. The method comprises providing to that person an alcoholic beverage comprising water and ethanol, wherein at least 5 mole percent of the ethanol is a deuterated alcohol according to Formula 1.

In another embodiment, the present invention provides a method of reducing the symptoms of alcohol-induced facial flushing in a person to whom the practitioner is serving alcoholic beverages. The method comprises providing to that person an alcoholic beverage comprising water and ethanol, wherein at least 5 mole percent of the ethanol is a deuterated alcohol according to Formula 1. Drinking beverages of the present invention is expected to provide for a reduction in disagreeable acetaldehydemia-related physical effects in the drinker, compared to the effects of drinking an equivalent amount of similar beverages where all the ethanol in the beverage is non-deuterated. This is especially true following the consumption of such beverages to an extent that ordinarily results in a hangover. Consumption of the instant beverages should typically reduce one or more hangover symptoms by at least 3 percent, as measured by a standardized scale in a human or animal model. Non-limiting symptoms associated with a hangover include dizziness, fatigue, headache, nausea, muscle aches, vomiting, sensitivity to bright light, and sensitivity to noise. Animal models related to such symptoms are described in R. D. Prediger et al. "Activation of adenosine A1 receptors reduces anxiety-like behavior during acute ethanol withdrawal (hangover) in mice." *Neuropsychopharmacology*, 2006, 31 (10):2210-2220; H. C. Becker, "Animal Models of Alcohol Withdrawal." *Alcohol Research & Health*, 2000, 24 (2):105-110.

Depending on the relative deuterium content and total amount of ethanol consumed, consumption of beverages according to the present invention will reduce one or more hangover symptoms by at least 5.0 percent, 7.5 percent or 10.0 percent. In favorable cases, such consumption reduces the symptoms by at least 15.0 percent, 20.0 percent or 25.0 percent.

Consumption of beverages according to the present invention furthermore should reduce one or more alcohol flush symptoms by at least 5 percent, as measured by a standardized scale in a human or animal model. Non-limiting symptoms associated with alcohol flush include skin redness, nausea, headaches, light-headedness, and increased pulse rate. Suitable measures of flushing are described, for example, in A. K. Kawata et al., "Flushing ASsessment Tool (FAST): psychometric properties of a new measure assessing flushing symptoms and clinical impact of niacin therapy," *Clinical Drug Investigation*, 2009, 29 (4):215-229.

Depending on the relative deuterium content and total amount of ethanol consumed, and upon the genotype and phenotype of the individual, consumption of the beverages and pharmaceutical compositions of the invention may reduce one or more alcohol flush symptoms by at least 5.0 percent, 7.5 percent or 10.0 percent. In favorable cases, such consumption reduces the symptoms by at least 15.0 percent, 20.0 percent or 25.0 percent.

Compositions of the present invention provide for new methods of marketing beverages containing alcohol. In one method, one communicates to a consumer that a beverage includes a particular amount of alcohol. One further communicates to the consumer that the alcohol in the beverage will provide for less disagreeable physical effects than a typical beverage including the particular amount of alcohol. The beverage comprises water and at least 1.0 percent of a deuterated alcohol according to Formula 1.

The consumer targeted by the method can be a person who wishes to decrease the deleterious side effects of a hangover; it can be a person having an enzyme abnormality related to the metabolism of ethanol; or it can be a person who is concerned about a different aspect of an alcohol-containing beverage. The compositions marketed according to this method include any composition encompassed by this document.

Experimental

The subject was a 52-year-old white Caucasian male, 154 kg, with no known abnormalities of ethanol metabolism. Experiments were conducted after an overnight fast. 1,1-Dideuterioethanol, 99 atom % D (CDN Isotopes; Quebec, Canada) (70 mL) was diluted to 500 mL with orange juice, and the resulting beverage was consumed by the subject over the course of five minutes. The mouth and palate were rinsed with orange juice, and data points were then obtained, in triplicate, every 10 minutes with a commercial breath analyzer (AlcoHAWK™ Pro, Q3 Innovations Inc., Independence, Iowa, U.S.A.) The control experiment employed 175 mL of commercial vodka (80 proof; 40% ethanol) but was otherwise identical.

Measured blood levels as a function of time are presented in FIG. 1. Each data point in the FIGURE is the average of the three measurements taken at each time point. The substantially equivalent areas under the curves suggest that the analyzer is equally sensitive to ordinary and deuterated ethanols.

The results from the control experiment are qualitatively similar to those reported by previous workers (see, e.g., Milne et al., *Am. J. Clin. Nutr.*, 1987, 46:688-693.) It is evident from FIG. 1, however, that the absorption of deuterated ethanol is substantially retarded, relative to ethanol having a natural isotopic abundance, and that the rate of clearance is reduced.

Numerous modifications and variations of the present invention are possible in light of the above teachings. It is

We claim:

1. A pharmaceutical composition comprising an active pharmaceutical ingredient and ethanol, wherein at least 5 mole percent of the ethanol is a deuterated alcohol having the formula

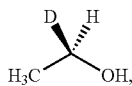

wherein each H may independently be hydrogen or deuterium.

2. The pharmaceutical composition of claim 1, wherein at least 5 mole percent of the ethanol is a deuterated alcohol having the formula

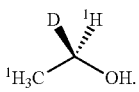

3. The pharmaceutical composition of claim 1, wherein at least 5 mole percent of the ethanol is a deuterated alcohol having the formula

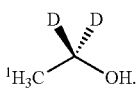

4. The pharmaceutical composition of claim 1, wherein at least 5 mole percent of the ethanol is a deuterated alcohol having the formula

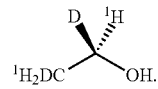

5. The pharmaceutical composition of claim 1, wherein at least 5 mole percent of the ethanol is a deuterated alcohol having the formula $CD_3CD_2OH$.

6. The pharmaceutical composition of claim 1, wherein at least 15 mole percent of the ethanol is said deuterated alcohol.

7. The pharmaceutical composition of claim 6, wherein at least 30 mole percent of the ethanol is said deuterated alcohol.

8. The pharmaceutical composition of claim 7, wherein at least 50 mole percent of the ethanol is said deuterated alcohol.

9. The pharmaceutical composition of claim 8, wherein at least 75 mole percent of the ethanol is said deuterated alcohol.

10. The pharmaceutical composition of claim 9, wherein at least 95 mole percent of the ethanol is said deuterated alcohol.

11. The pharmaceutical composition of claim 1, wherein from 1 to 40% by weight of the composition is ethanol.

12. The pharmaceutical composition of claim 1, wherein from 0.25 to 60% by weight of the composition is deuterated ethanol.

13. The pharmaceutical composition of claim 1, wherein from 50 to 100% by weight of the ethanol in the composition is deuterated ethanol.

14. The pharmaceutical composition of claim 1, further comprising: water.

15. The pharmaceutical composition of claim 1, further comprising: a pharmaceutically acceptable excipient.

16. The pharmaceutical composition of claim 1, further comprising: water and a pharmaceutically acceptable excipient.

* * * * *